US011311261B2

(12) United States Patent
Hsieh et al.

(10) Patent No.: US 11,311,261 B2
(45) Date of Patent: Apr. 26, 2022

(54) NUCLEAR IMAGE PROCESSING METHOD

(71) Applicant: INSTITUTE OF NUCLEAR ENERGY RESEARCH, ATOMIC ENERGY COUNCIL, EXECUTIVE YUAN, Taoyuan (TW)

(72) Inventors: Ho-Hui Hsieh, Taichung (TW); Yu-Ching Ni, Taoyuan (TW)

(73) Assignee: INSTITUTE OF NUCLEAR ENERGY RESEARCH, ATOMIC ENERGY COUNCIL, EXECUTIVE YUAN, Taoyuan (TW)

( * ) Notice: Subject to any disclaimer, the term of this patent is extended or adjusted under 35 U.S.C. 154(b) by 530 days.

(21) Appl. No.: 16/428,510

(22) Filed: May 31, 2019

(65) Prior Publication Data

US 2020/0315563 A1    Oct. 8, 2020

(30) Foreign Application Priority Data

Apr. 3, 2019  (TW) .................................. 108111998

(51) Int. Cl.
| G06K 9/62 | (2006.01) |
| A61B 6/00 | (2006.01) |
| A61B 5/00 | (2006.01) |
| A61B 6/03 | (2006.01) |
| G06V 10/32 | (2022.01) |

(52) U.S. Cl.
CPC ............ *A61B 6/501* (2013.01); *A61B 5/7267* (2013.01); *A61B 6/037* (2013.01); *A61B 6/5205* (2013.01); *G06K 9/6256* (2013.01); *G06K 9/6263* (2013.01); *G06V 10/32* (2022.01); *G06V 2201/03* (2022.01)

(58) Field of Classification Search
CPC .............................. A61B 6/501; A61B 5/7267
See application file for complete search history.

(56) References Cited

U.S. PATENT DOCUMENTS

| 8,674,315 B2 * | 3/2014 | Vija | ...................... G06T 11/008 |
| | | | 250/370.08 |
| 10,255,696 B2 * | 4/2019 | Wang | .................... G06T 11/006 |

OTHER PUBLICATIONS

Ho-Hui Hsieh, Multicenter normalization of Tc-99m-ECD brain SPECT image by few normal control data, 58th Annual Meeting of the Japanese Society of Nuclear Medicine, Nov. 16, 2018, 15 pages.

* cited by examiner

*Primary Examiner* — Tuan H Nguyen
(74) *Attorney, Agent, or Firm* — Muncy, Geissler, Olds & Lowe, P.C.

(57) ABSTRACT

A nuclear image processing method is provided. The method includes the following steps: inputting a normalized standard space nuclear image; selecting a voxel of the normalized standard space nuclear image and collecting the values of the neighbor voxels to form a voxel value set; conducting a data augmentation algorithm to generate a voxel distribution function; calculating an expected value of the distribution and calculating a first standard deviation of the portion over the expected value and a second standard deviation of the portion lower than the expected value; repeating the above steps to calculate the expected value, the first standard deviation and the second standard deviation of the necessary voxels, so as to form an image standardization template set including expected value template, first standard deviation template and the second standard deviation template.

10 Claims, 6 Drawing Sheets
(1 of 6 Drawing Sheet(s) Filed in Color)

NUCLEAR IMAGE PROCESSING METHOD

CROSS-REFERENCE TO RELATED APPLICATIONS

This application claims priority from Taiwan Patent Application No. 108111998, filed on Apr. 3, 2019, in the Taiwan Intellectual Property Office, the content of which is hereby incorporated by reference in its entirety for all purposes.

BACKGROUND OF THE INVENTION

1. Field of the Invention

The present disclosure generally relates to a nuclear image processing method, and in particular, to a process method for generating an image standardization template set by a data augmentation algorithm and correcting and enhancing a patient image to generate a standard nuclear image crossing hospitals and different examination instruments.

2. Description of the Related Art

The nuclear medicine is a medical specialty that uses radioisotopes and their labeled drugs (collectively referred to as radiopharmaceuticals) to diagnose, treat, and study human diseases. Among them, nuclear medicine is to send a very small amount of radiopharmaceuticals into the subject by intravenous injection, oral or inhalation, and then detect the absorption, the metabolism and the distribution of the drug in the whole body or specific organ tissues by a nuclear medicine imaging instrument. Finally, the nuclear medicine specialist will interpret the report and provide it to the clinician as a reference for diagnosis, treatment and treatment planning. For example, the nuclear medicine imaging examination for the brain is an important reference indicator with discriminating power in the diagnosis process of dementia. Early diagnosis can also be provided for diseases such as cerebral circulation disorder, cerebral circulation disorder caused by head trauma, Alzheimer's disease, brain stroke, cerebral ischemia, brain tumor, epilepsy and the like.

However, due to the limitations of the examination process and instruments, such as used dosage of radiopharmaceuticals and the difference in imaging quality of different brand instruments, the examination of nuclear medicine still has many problems in interpretation. The same patient may produce different images under the examination of different hospitals and different brand instruments, and the quality of the generated images may not be sufficient to provide medical interpretation, thus resulting in inconsistent final interpretation results. Moreover, the current interpretation still relies on nuclear medicine specialists for manual interpretation. The subjective experience has a high degree of influence on the interpretation results, and the possibility of misjudgment or missed judgment is relatively increased. The technique of artificial intelligence is combined and the image interpretation can be conducted by the machine. When the above image quality cannot be consistent, it is difficult to standardize the image data for providing machine learning and the accuracy of the interpretation result cannot reach the required level. Therefore, the current nuclear medicine examination still cannot use machine learning to complete the interpretation of nuclear images in a simplified and accurate manner.

In view of this, how to establish a nuclear image processing method, which can read the original nuclear medicine image, convert it to form an enhanced image that meet the standard, and provide data for machine learning to improve the interpretation result through effective training, should be the goal that the relevant nuclear medicine specialist hopes to achieve. Hence, the inventor provides the nuclear image processing method to resolve the drawbacks so as to promote the practicability.

SUMMARY OF THE INVENTION

In view of the aforementioned technical problems, one objective of the present disclosure provides a nuclear image processing method, which is capable of resolving the technical problem of poor quality of the nuclear images, errors of correction, and unable to establish an automatic interpretation mechanism.

In accordance with one objective of the present disclosure, a nuclear image processing method is provided. The nuclear image processing method includes the following steps of: inputting a normalized standard space nuclear image by an input device, the normalized standard space nuclear image being stored in a storage device; selecting a voxel of the normalized standard space nuclear image and collecting values of a plurality of neighbor voxels to form a voxel value set by a processor; conducting a data augmentation algorithm by the processor, data of the voxel value set being increased to generate a voxel distribution function; calculating an expected value of a distribution relationship of the voxel distribution function and calculating a first standard deviation of a portion over the expected value and a second standard deviation of a portion lower than the expected value by the processor; repeating the above steps by the processor to calculate the expected value, the first standard deviation and the second standard deviation of a plurality of necessary voxels, and filling in the normalized standard space nuclear image to form an image standardization template set including an expected value template, a first standard deviation template and a second standard deviation template.

Preferably, the normalized standard space nuclear image may be formed by acquiring an original nuclear medicine image by a nuclear medicine examination instrument and providing conversions of a brain spatial normalization and a drug concentration to image count normalization.

Preferably, the nuclear image processing method may further include the following step of: acquiring a patient image by the nuclear medicine examination instrument, forming a patient normalized standard space nuclear image by the conversion of the brain spatial normalization and the drug concentration to image count normalization; inputting the patient normalized standard space nuclear image by the input device and storing in the storage device; extracting the image standardization template set of the nuclear medicine examination instrument and calculating a difference between the patient normalized standard space nuclear image and the expected value template by the processor; extracting a target image standardization template and calculating a template difference between the image standardization template set and the target image standardization template by the processor; correcting the difference based on the first standard deviation template, the second standard deviation template and the template difference to generate an image abnormal score by the processor.

Preferably, the image abnormal score may be used to mark the patient normalized standard space nuclear image for generating an abnormal enhanced image.

Preferably, the image abnormal score and the abnormal enhanced image may be stored in the storage device and outputted by an output device for providing a medical doctor to interpret the image abnormal score and the abnormal enhanced image.

Preferably, the image abnormal score, the abnormal enhanced image and the interpretation results may be stored in a nuclear medicine image database and an automatic image classification and an interpretation mechanism may be established through a training process by a machine learning algorithm.

Preferably, the original nuclear medicine image and the patient image may include a single photon emission computed tomography (SPECT) image or a positron emission tomography (PET) image.

Preferably, the difference of a portion greater than zero may be corrected by the first standard deviation template to generate an abnormal decay image and the difference of a portion smaller than zero may be corrected by the second standard deviation template to generate an abnormal active image, the abnormal decay image and the abnormal active image are combined as the abnormal enhanced image.

Preferably, the data augmentation algorithm may include a bootstrap bagging algorithm and a probability sampling algorithm.

Preferably, the expected value may include a median value or an average value.

As mentioned previously, the nuclear image processing method in accordance with the present disclosure may have one or more advantages as follows.

1. The nuclear image processing method may establish the image standardization template for different hospitals and different brands of nuclear medicine examination instrument by using the bootstrap bagging algorithm, which can be obtained by extracting image data of only a small number of healthy people. The effective standard image processing mechanism can be established accordingly to improve the nuclear image analysis efficiency.

2. The nuclear image processing method is capable of converting the cross-hospitals or cross-instruments image to a nuclear enhanced image with consistent standard by the standardization score algorithm. The method not only improves the image quality to the doctors for providing the interpretation, but also makes sure the accuracy of the interpretation.

3. The nuclear image processing method is capable of providing the image data by establishing the standard template and the process steps of improving abnormal enhanced image, which are suitable of conducting machine learning. The database of the related nuclear image data becomes more complete and the machine learning cost can be reduced.

Furthermore, the automatic interpretation to the nuclear image may have higher reliability.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE PREFERRED EMBODIMENTS

In order to facilitate the understanding of the technical features, the contents and the advantages of the present disclosure, and the effectiveness thereof that can be achieved, the present disclosure will be illustrated in detail below through embodiments with reference to the accompanying drawings. On the other hand, the diagrams used herein are merely intended to be schematic and auxiliary to the specification, but are not necessary to be true scale and precise configuration after implementing the present disclosure. Thus, it should not be interpreted in accordance with the scale and the configuration of the accompanying drawings to limit the scope of the present disclosure on the practical implementation.

In accordance with the embodiment(s) of the present invention, the components, process steps, and/or data structures described herein may be implemented using various types of operating systems, computing platforms, computer programs, and/or general purpose machines. In addition, those of ordinary skill in the art will recognize that devices of a less general purpose nature, such as hardwired devices, field programmable gate arrays (FPGAs), application specific integrated circuits (ASICs), or the like, may also be used without departing from the scope and spirit of the inventive concepts disclosed herein. Where a method comprising a series of process steps is implemented by a computer or a machine and those process steps can be stored as a series of instructions readable by the machine, they may be stored on a tangible medium such as a computer memory device (e.g., ROM (Read Only Memory), PROM (Programmable Read Only Memory), EEPROM (Electrically Erasable Programmable Read Only Memory), FLASH Memory, Jump Drive, and the like), magnetic storage medium (e.g., tape, magnetic disk drive, and the like), optical storage medium (e.g., CD-ROM, DVD-ROM, paper card and paper tape, and the like) and other known types of program memory.

Figure 1:
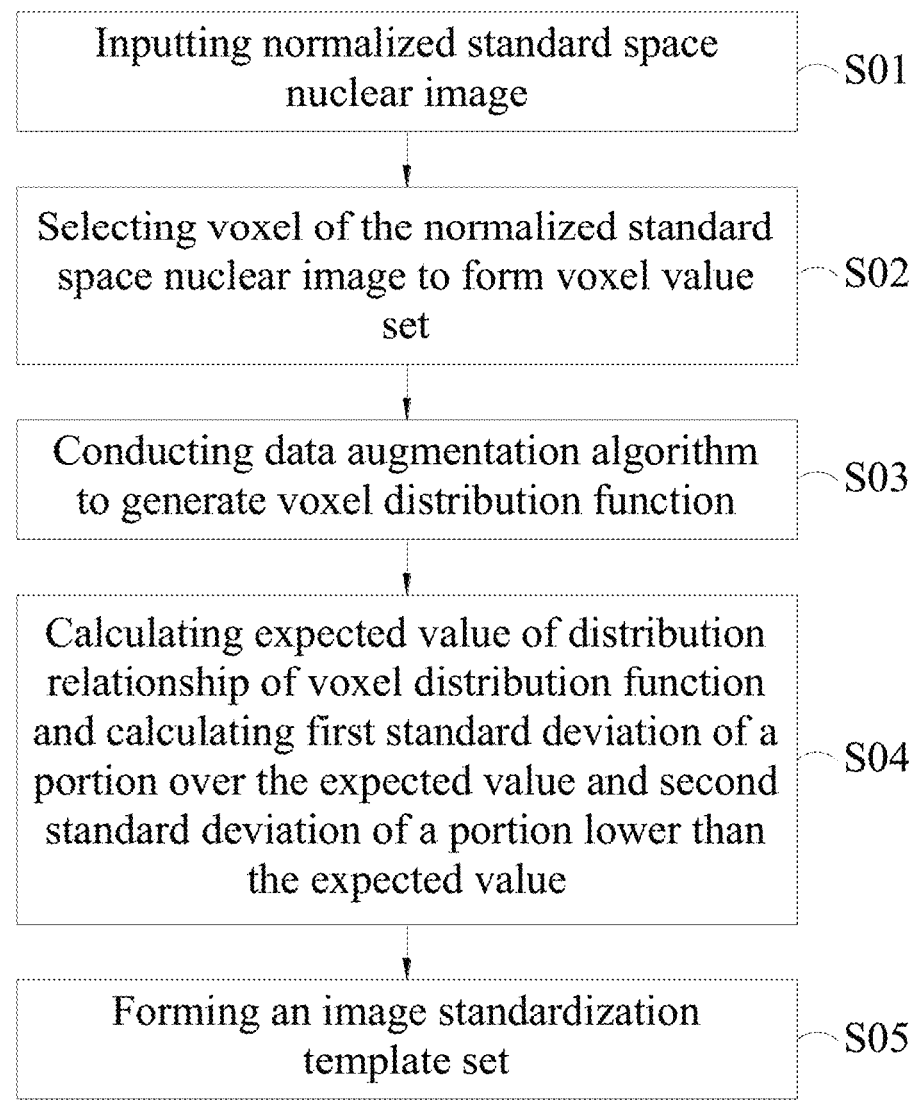
FIG. 1 is a flow chart of a nuclear image processing method in accordance with the present disclosure.

FIG. 1 is a flow chart of a nuclear image processing method in accordance with the present disclosure. As shown in the figure, the nuclear image processing method includes the following steps (S01-S05):

Step S01: Inputting normalized standard space nuclear image. Firstly, the normalized standard space nuclear image is obtained by acquiring an original nuclear medicine image of a healthy person by a nuclear medicine examination instrument. For example, a single photon emission computed tomography (SPECT) or a positron emission tomography (PET) can be used. A gamma-ray generated by the nuclear medicine is used to conduct the detection and the imaging, so as to form a single photon emission computed tomography (SPECT) image or a positron emission tomography (PET) image. In the present embodiment, the Tc-99m-

ECD brain single photon computed tomography image of the cerebral blood flow tomography may be used to describe the present method. However, the present disclosure is not limited in such an image. Other tomography or planar nuclear imaging images are also suitable for the treatment of the present disclosure. As mentioned in the prior art, the different brand instruments and the different examination process may cause different results. Thus, the original nuclear medicine image acquired by the nuclear medicine examination instrument will be provided with conversions of a brain spatial normalization and a drug concentration to image count normalization. The brain spatial normalization means that each brain image is relocated according to the standard definition of an anatomical location. In other words, the original nuclear medicine image is converted to a brain mapping and adjusted the pixel value according to the drug concentration, so as to form the normalized standard space nuclear image. After the normalized standard space nuclear image is obtained, the normalized standard space nuclear image can be inputted by an input device and stored in the storage device. The input device may be a computer device. The file of the normalized standard space nuclear image is received through a computer interface or a network interface. The file can be saved in the storage device, such as the memory of the computer, the storage media or the server database. In addition, the input device may also directly connect to the nuclear medicine examination instrument for receiving the original nuclear medicine image and conduct the conversion of image mapping and count normalization through the computer software program, so as to generate the normalized standard space nuclear image.

Figure 2:
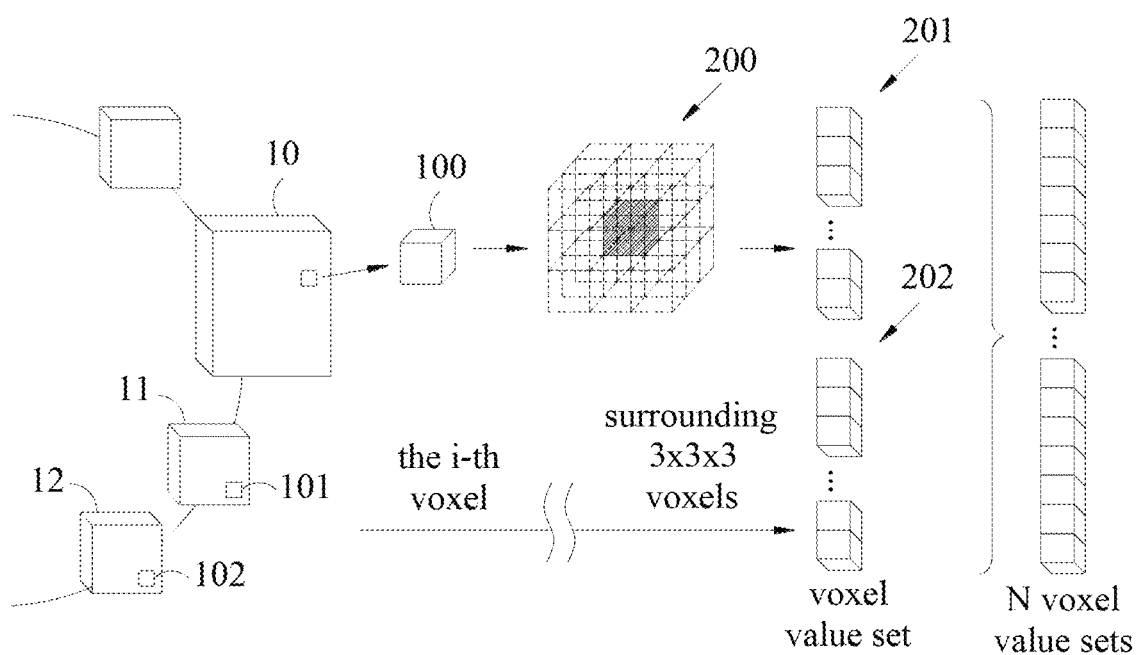
FIG. 2 is the schematic diagram illustrating the voxel of the standard nuclear image in accordance with the present disclosure.

Step S02: Selecting voxel of the normalized standard space nuclear image to form voxel value set. In this step, the computer device for conducting nuclear image analysis may execute a series of operation commands by a processor to select a voxel of the normalized standard space nuclear image and collect the values of a plurality of neighbor voxels to form the voxel value set. The processor may include central processing unit (CPU), microprocessor, multi-core processor, graphic processor. The present embodiment takes voxel i for example. Please refer FIG. 2, which is the schematic diagram illustrating a voxel of a standard nuclear image in accordance with the present disclosure. As shown in the figure, the i-th voxel 100 is selected as a center from the normalized standard space nuclear image 10 and the values of the neighbor voxels 200 around the voxel 100 are collected. That is, taking voxel 100 as the center with a size of 3×3×3 voxels, and collecting the values of the other 26 voxels around the voxel 100, so as to form the i-th voxel value set 201. Then, the i-th voxel 101 is selected as a center from the second normalized standard space nuclear image 11. The above steps are repeated to form the second voxel value set 202. Furthermore, the i-th voxel 102 is selected as a center from the third normalized standard space nuclear image 12, until all the i-th voxel of the provided normalized standard space nuclear image finish the above processes and generate N voxel value sets. The present embodiment chooses cube structure as the range of the voxel. However, the present disclosure is not limited in such structure. The sphere or the other shapes of the structures can be used as the range for collecting the voxel. As long as it does not exceed the image range, it can be applied to the operation steps of the present disclosure.

Figure 3:
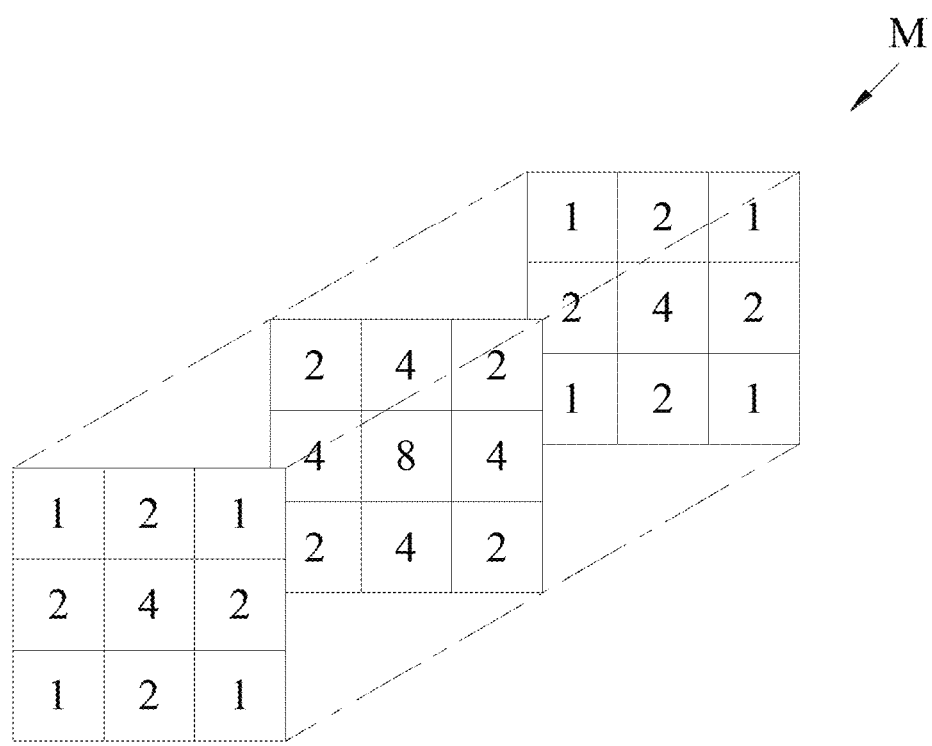
FIG. 3 is the schematic diagram of a probability matrix in accordance with the present disclosure.

Step S03: Conducting data augmentation algorithm to generate voxel distribution function. After the N voxel value sets are generated, the processor may execute the commands to conduct the data augmentation algorithm. The data of the N voxel value sets is increased to generate a voxel function after data increment. The present embodiment uses a bootstrap bagging algorithm and a probability sampling algorithm as the example. Wherein the bootstrap bagging algorithm includes the step of sampling each group of the voxel value set according to the probability value in its probability matrix, so as to obtain the first voxel function. Once again, sampling each group of the voxel value set according to the probability value in its probability matrix, so as to obtain the second voxel function. Repeat the process W times to obtain W voxel functions. The W voxel functions are integrated into a new voxel function F according to the expected value. Please refer FIG. 3, which is the schematic diagram of a probability matrix in accordance with the present disclosure. As shown in the figure, the probability matrix M is a 3×3×3 matrix and the 27 locations may represent the locations of the voxel and the 26 neighbor voxels. The values in the probability matrix M indicate the probability of sampling the voxel value.

Figure 4:
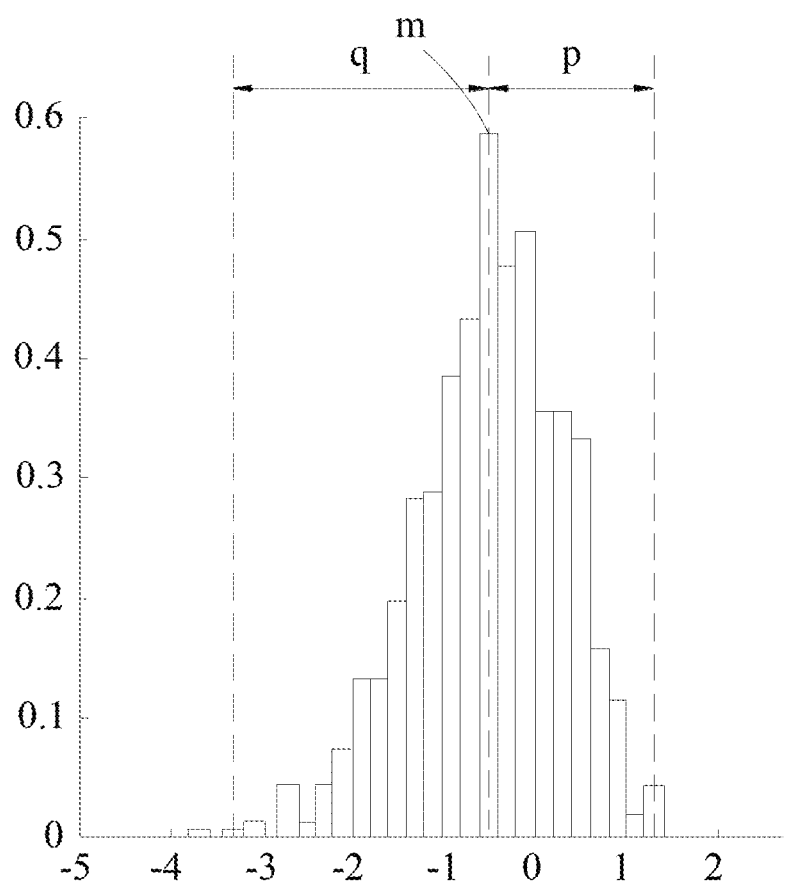
FIG. 4 is the schematic diagram of a voxel distribution function in accordance with the present disclosure.

Step S04: Calculating expected value of distribution relationship of voxel distribution function and calculating first standard deviation of a portion over the expected value and second standard deviation of a portion lower than the expected value. Please refer FIG. 4, which is the schematic diagram of a voxel distribution function in accordance with the present disclosure. As shown in the figure, the present embodiment uses the median value as the expected value. The present disclosure is not limited in that. In other embodiments, the average value can be used for the calculation. Referring the distribution of the new voxel function F obtained by the above steps, most of its data is obliquely distributed and not a normal distribution with a mean of zero. Therefore, the present embodiment calculates the median value m. In the distribution relationship of voxel distribution function, the variance p of a portion over the median value m and the variance q of a portion lower than the median value m. The variance p and q are the variance of two semi-normal distribution functions, and then convert to the first standard deviation $\sigma p$ and the second standard deviation $\sigma q$ respectively.

Step S05: Forming an image standardization template set. The above steps are repeated to calculate the expected value, the first standard deviation and the second standard deviation of a plurality of necessary voxels, and filling in the normalized standard space nuclear image to form an image standardization template set including an expected value template, a first standard deviation template and a second standard deviation template. The image standardization template set is saved in the storage device. Continuing the above embodiment for calculating the median value m, the first standard deviation $\sigma p$ over the median value m and the second standard deviation $\sigma q$ lower than the median value m. The processor further executes the above steps to obtain the median value and the standard deviation of the other necessary voxels and sequentially fills in the normalized standard space nuclear image, so as to generate a median value template Mt, a first standard deviation template $\Sigma p$ and a second standard deviation template $\Sigma q$. The image standardization template set (Mt、$\Sigma p$、$\Sigma q$) is saved in the storage device. The storage device here can be the same as the storage device that originally stored the normalized standard space nuclear image. The storage device may also independently design as the cloud database for saving the image standardization template set of the healthy image. When the local hospitals conduct nuclear medicine imaging examinations, it is able to connect to the cloud database for accessing the image standardization template set, which may be a calibration standard for adjusting and enhancing images. The relevant processing steps will be further described in the following paragraphs.

Figure 5:
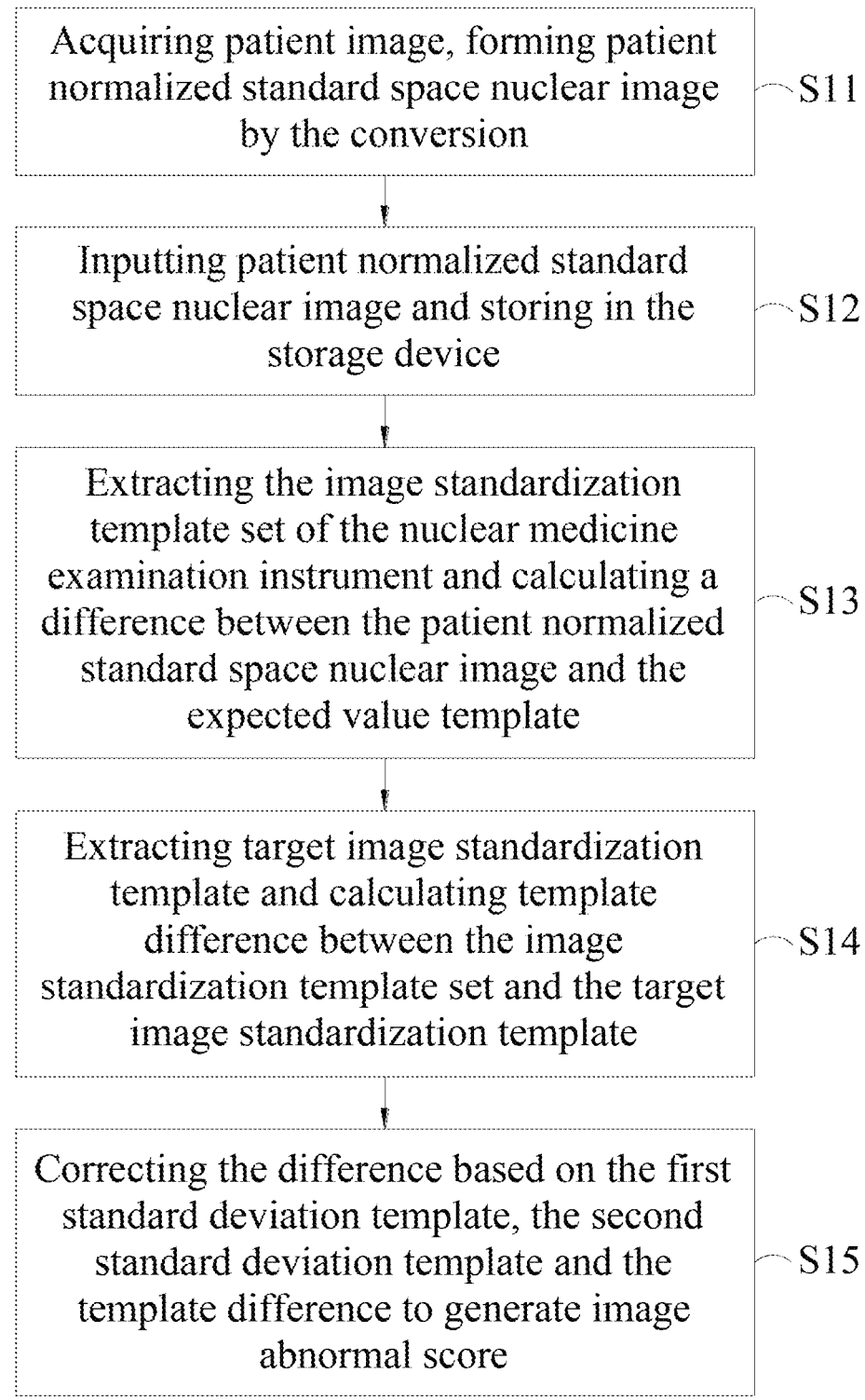
FIG. 5 is a flow chart of a nuclear image enhancing method in accordance with the present disclosure.

FIG. 5 is a flow chart of a nuclear image enhancing method in accordance with the present disclosure. As shown in the figure, the nuclear image enhancing method includes the following steps (S11-S15):

Step S11: Acquiring patient image, forming patient normalized standard space nuclear image by the conversion. When the patient conducts the nuclear medicine examination, the image is acquired by the nuclear medicine examination instrument. The patient image is similar to the original nuclear medicine image of the healthy person mentioned in step S01. Therefore, the same conversion of the brain spatial normalization and the drug concentration to image count normalization are performed to form the patient normalized standard space nuclear image.

Step S12: Inputting patient normalized standard space nuclear image and storing in the storage device. The patient normalized standard space nuclear image obtained by the previous step may be obtained by the input device of the computer. The patient normalized standard space nuclear image is saved in the storage device.

Step S13: Extracting the image standardization template set of the nuclear medicine examination instrument and calculating a difference between the patient normalized standard space nuclear image and the expected value template. Since the different hospitals and different brands of nuclear medicine examination instrument may have differences in the characteristics of the imaging, the pre-storing image standardization template is required for the image correction. The different nuclear medicine examination instruments may use the method of the previous embodiment to generate the image standardization template set according to the nuclear image of the healthy person. For example, the image standardization template set (Mt、$\Sigma p$、$\Sigma q$) mentioned in the previous embodiment. In possession of the template standard corresponding to the nuclear medicine examination instrument, the computer device mat calculate the difference $\Delta I=(Mt-I)$ between the patient normalized standard space nuclear image I and the median value template Mt.

Step S14: Extracting target image standardization template and calculating template difference between the image standardization template set and the target image standardization template. In addition to verifying the difference in the patient normalized standard space nuclear image I according to the image standardization template set of the actual examination instrument, the target image standardization template is extracted to enable cross-hospital and cross-machine nuclear images to find a consistent judgment criteria and improve the quality of data for machine learning. The target image standardization template may be the standard established by the medical center or the nuclear image analysis center, which meets the recommended specifications for nuclear image and is provided as the correction standard for other hospital or other examination instrument. In the present application, the computer device may connect to the target image database in the cloud server to access the target image standardization template stored in the database. The template difference bias=$(Mt-M_c)$ is calculated by checking the difference between the median value template Mt among the image standardization template set of the corresponding examination instrument and the median value template $M_c$ of the target image standardization template. That is, the median value template $M_c$ of the target image standardization template is used to correct the patient image.

Step S15: Correcting the difference based on the first standard deviation template, the second standard deviation template and the template difference to generate image abnormal score. In the present application, the processor executes the commands to divide the difference $\Delta I$ into two parts including a portion greater than zero and the other portion smaller than zero and correct the difference $\Delta I$ according to the first standard deviation template $\Sigma p$, the second standard deviation template $\Sigma q$ and the template difference bias. In the portion that the difference $\Delta I$ greater than zero, the difference is corrected by the first standard deviation template $\Sigma p$ and the template difference bias, so as to generate an abnormal decay image $I_{dec}=(Mt-bias-I)/\Sigma p$. Relatively, in the portion that the difference $\Delta I$ smaller than zero, the difference is corrected by the second standard deviation template $\Sigma q$ and the template difference bias, so as to generate an abnormal active image $I_{inc}=(Mt-bias-I)/\Sigma q$. The above image values may be used as the image abnormal score, which are provided for the doctor to generate the interpretation of the abnormal decay portion and the abnormal active portion.

Figure 6:
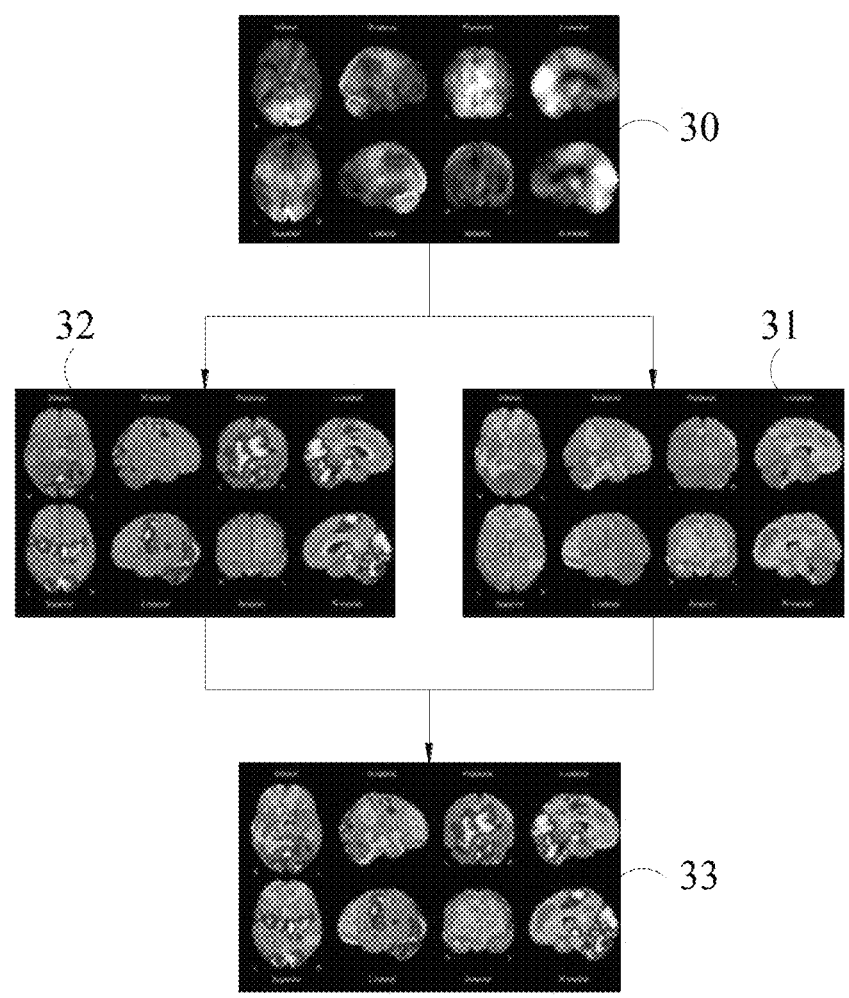
FIG. 6 is the schematic diagram of nuclear images before and after image enhancement in accordance with the present disclosure.

The abnormal score mentioned above may be used to mark the patient normalized standard space nuclear image according the range of the values. Please refer to FIG. 6, which is the schematic diagram of nuclear images before and after image enhancement in accordance with the present disclosure. As shown in the figure, through the above calculation steps, the patient normalized standard space nuclear image 30 of patient's brain can be marked by colors using the values of the abnormal decay image $I_{dec}$, so as to form a brain abnormal decay image 31. On the other side, the image may also be marked by colors using the values of the abnormal active image $I_{inc}$, so as to form a brain abnormal active image 32. Furthermore, the abnormal decay image $I_{dec}$ and the abnormal active image $I_{inc}$ may be further combined to form an improved abnormal standard score Z=merge ($I_{dec}$, $I_{inc}$). The corresponding scores may also be combined to form a brain function abnormal enhanced image 33. The image abnormal score or the abnormal enhanced image with color marks added may be saved in the storage device and uploaded to the doctor through the output device, such as the computer, the display or the mobile phone, so as to assist the doctor for interpreting the nuclear image.

In the present application, the nuclear tomography image of blood flow in the brain of patients may be adjusted according to the template of the nuclear medicine examination instrument and the target image standardization template. The abnormal enhanced image generated based on the above process steps may improve the qualities of data and image. Most important, the abnormal enhanced image is corrected by the same template, so that the interpretation can have consistent standard. Thus, after obtaining the abnormal enhanced image and the interpretation result made by the doctor, such information can be stored in the nuclear image database. That is, the collected standardized data can be used in the computer device for conducting the training process of machine learning. After the automatic classification and interpretation mechanism is established, the following patient's nuclear image may conduct an automatic interpretation by the artificial intelligent method. To improve the consistent interpretation also reduces the subjective error caused by manual interpretation. On the other hand, since the data required in the machine learning have already converted into a standardized normal distribution relationship by the process method disclosed in the present disclosure, the learning efficiency and the accuracy can be improved during the machine learning process.

For example, the standardized nuclear image may conduct feature extraction by using the convolutional neural network. However, the present disclosure is not limited in such method. The other machine learning methods may also suitable for the nuclear image processing method defined in the present disclosure. The convolutional neural network may include combination and calculation of one or more convolution layers, pooling layers and inception layers, so as to obtain the image features of the nuclear image. Then, the actual classification of the interpretation results are used for training, so that the deep learning network can be used in the analysis and interpretation of the nuclear image.

While the means of specific embodiments in present disclosure has been described by reference drawings, numerous modifications and variations could be made thereto by those skilled in the art without departing from the scope and spirit of the disclosure set forth in the claims. The modifications and variations should in a range limited by the specification of the present disclosure.

What is claimed is:

1. A nuclear image processing method, comprising the following steps of:
    inputting a normalized standard space nuclear image by an input device, the normalized standard space nuclear image being stored in a storage device;
    selecting a voxel of the normalized standard space nuclear image and collecting values of a plurality of neighbor voxels to form a voxel value set by a processor;
    conducting a data augmentation algorithm by the processor, data of the voxel value set being increased to generate a voxel distribution function;
    calculating an expected value of a distribution relationship of the voxel distribution function and calculating a first standard deviation of a portion over the expected value and a second standard deviation of a portion lower than the expected value by the processor;
    repeating the above steps by the processor to calculate the expected value, the first standard deviation and the second standard deviation of a plurality of necessary voxels, and filling in the normalized standard space nuclear image to form an image standardization template set including an expected value template, a first standard deviation template and a second standard deviation template.

2. The nuclear image processing method of claim 1, wherein the normalized standard space nuclear image is formed by acquiring an original nuclear medicine image by a nuclear medicine examination instrument and providing conversions of a brain spatial normalization and a drug concentration to image count normalization.

3. The nuclear image processing method of claim 2, further comprising the following step of:
    acquiring a patient image by the nuclear medicine examination instrument, forming a patient normalized standard space nuclear image by the conversion of the brain spatial normalization and the drug concentration to image count normalization;
    inputting the patient normalized standard space nuclear image by the input device and storing in the storage device;
    extracting the image standardization template set of the nuclear medicine examination instrument and calculating a difference between the patient normalized standard space nuclear image and the expected value template by the processor;
    extracting a target image standardization template and calculating a template difference between the image standardization template set and the target image standardization template by the processor;
    correcting the difference based on the first standard deviation template, the second standard deviation template, and the template difference to generate an image abnormal score by the processor.

4. The nuclear image processing method of claim 3, wherein the image abnormal score is used to mark the patient normalized standard space nuclear image for generating an abnormal enhanced image.

5. The nuclear image processing method of claim 4, wherein the image abnormal score and the abnormal enhanced image are stored in the storage device and outputted by an output device for providing a medical doctor to interpret the image abnormal score and the abnormal enhanced image.

6. The nuclear image processing method of claim 5, wherein the image abnormal score, the abnormal enhanced image, and the interpretation results are stored in a nuclear medicine image database and an automatic image classification and an interpretation mechanism are established through a training process by a machine learning algorithm.

7. The nuclear image processing method of claim 4, wherein the difference of a portion greater than zero is corrected by the first standard deviation template to generate an abnormal decay image and the difference of a portion smaller than zero is corrected by the second standard deviation template to generate an abnormal active image, the abnormal decay image and the abnormal active image are combined as the abnormal enhanced image.

8. The nuclear image processing method of claim 3, wherein the original nuclear medicine image and the patient image comprise a single photon emission computed tomography image or a positron emission tomography image.

9. The nuclear image processing method of claim 1, wherein the data augmentation algorithm comprises a bootstrap bagging algorithm and a probability sampling algorithm.

10. The nuclear image processing method of claim 1, wherein the expected value comprises a median value or an average value.

* * * * *